United States Patent
He et al.

(10) Patent No.: US 10,227,656 B2
(45) Date of Patent: Mar. 12, 2019

(54) DIAGNOSTIC/PROGNOSTIC MARKER AND THERAPEUTIC TARGET FOR CANCER

(71) Applicant: Baylor College of Medicine, Houston, TX (US)

(72) Inventors: Bin He, Bellaire, TX (US); Rainer B. Lanz, Houston, TX (US); Nicholas Mitsiades, Boston, MA (US); Qin Feng, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 15/034,467

(22) PCT Filed: Nov. 7, 2014

(86) PCT No.: PCT/US2014/064600
§ 371 (c)(1),
(2) Date: May 4, 2016

(87) PCT Pub. No.: WO2015/070045
PCT Pub. Date: May 14, 2015

(65) Prior Publication Data
US 2016/0281170 A1   Sep. 29, 2016

Related U.S. Application Data

(60) Provisional application No. 61/901,563, filed on Nov. 8, 2013.

(51) Int. Cl.
*C12Q 1/6886* (2018.01)
*G01N 33/574* (2006.01)

(52) U.S. Cl.
CPC ....... *C12Q 1/6886* (2013.01); *G01N 33/5748* (2013.01); *G01N 33/57415* (2013.01); *G01N 33/57434* (2013.01); *G01N 33/57496* (2013.01); *C12Q 2600/106* (2013.01); *C12Q 2600/118* (2013.01); *C12Q 2600/158* (2013.01); *G01N 2333/4703* (2013.01)

(58) Field of Classification Search
CPC .......................... C12Q 1/6886; G01N 33/574
USPC ........................................................ 435/7.23
See application file for complete search history.

(56) References Cited

U.S. PATENT DOCUMENTS

| | | |
|---|---|---|
| 2005/0181370 A1 | 8/2005 | De Smet et al. |
| 2005/0230149 A1 | 10/2005 | Boucher et al. |
| 2006/0008468 A1 | 1/2006 | Chiang et al. |
| 2011/0290559 A1 | 12/2011 | Rodney et al. |
| 2013/0120154 A1 | 5/2013 | Gleitman |
| 2013/0244256 A1 | 9/2013 | Clarke et al. |
| 2013/0296328 A1 | 11/2013 | Fuks et al. |

FOREIGN PATENT DOCUMENTS

| | | |
|---|---|---|
| WO | 2012152811 A1 | 11/2012 |
| WO | 2013041731 A1 | 3/2013 |

OTHER PUBLICATIONS

Boormans et al. (Int. J. Cancer, published online Jan. 15, 2013, 133: 335-346).*
Yu, Jindan, et al; "An Integrated Network of Androgen Receptor, Polycomb, and TMPRSS2-ERG Gene Fusions in Prostate Cancer Progression"; National Institutes of Health, Cancer Cell. May 18, 2010: 17(5); 443-454.
Taylor, Barry S., et al; "Integrative Genomic Profiling of Human Prostate Cancer;"; National Institutes of Health; Cancer Cell. Jul. 13, 2010; 18(1): 11-22.
Jhavar, Sameer et al; "Detection of TMPRSS2-ERG Translocations in Human Prostate Cancer by Expression Profiling Using GeneChip Human Exon 1.0 ST Arrays"; Journal of Molecular Diagnostics vol. 10, No. 1, Jan. 2008.
Boormans, J.L. et al; Prognostic Implications of Important Genetic Alterations in Prostate Cancer; Erasmus University Rotterdam; Feb. 18, 2011.
Tomlins, Scott A., et al; "Recurrent Fusion of TMPRSS2 and ETS Transcription Factor Genes in Prostate Cancer"; Science; Oct. 28, 2005, vol. 310.
Boormans, Joost, et al; "Identification of the Novel Prostate Cancer Biomarker TDRD1 as a Direct Target Gene of ERG in Primary Prostate Cancer"; Prostate Cancer: Basic Research III; American Urological Association Meeting; May 20, 2012.

* cited by examiner

*Primary Examiner* — Yan Xiao
(74) *Attorney, Agent, or Firm* — Norton Rose Fulbright US LLP

(57) ABSTRACT

Embodiments of the present disclosure concern methods and compositions for prognosis, diagnosis, and/or treatment of prostate cancer or breast cancer, for example. Certain embodiments of the disclosure concern assaying for the expression level of TDRD1. Particular embodiments concern treating an individual with a particular cancer therapy when the expression level of TDRD1 is overexpressed.

6 Claims, 9 Drawing Sheets

DIAGNOSTIC/PROGNOSTIC MARKER AND THERAPEUTIC TARGET FOR CANCER

This application is a national phase application under 35 U.S.C. § 371 that claims priority to International Application No. PCT/US2014/064600 filed Nov. 7, 2014 which claims priority to U.S. Provisional Patent Application Ser. No. 61/901,563, filed Nov. 8, 2013, all of which are incorporated by reference herein in their entirety.

STATEMENT REGARDING FEDERALLY SPONSORED RESEARCH OR DEVELOPMENT

This invention was made with government support under DK081446 awarded by NIH/NIDDK. The government has certain rights in the invention.

TECHNICAL FIELD

Embodiments of the disclosure concern at least the fields of medicine, cell biology, molecular biology, diagnostics and gene expression analysis.

BACKGROUND

One of the holy grails of cancer research is to identify tumors that need to be aggressively treated. For prostate cancer, for example, after decades of intensive research, there is still no prognostic marker to distinguish between indolent and aggressive tumors. There is no reliable way to identify which tumors need to be treated aggressively and which do not need aggressive treatment. Therefore, the importance of finding a clinically relevant prognostic marker for prostate cancer cannot be over-estimated.

TMPRSS2-ERG fusion, caused by a chromosomal translocation, occurs in ~50% of primary prostate tumors and results in over-expression of a truncated but functional erythroblast transformation-specific (ETS)-related gene (ERG) in prostate tumors. It is believed that oncogenic ERG is the driver of prostate tumorigenesis. ERG is a member of the ETS family of transcription factors. It contains an ETS DNA-binding domain and can directly regulate target gene expression. However, the inventors reasoned that, as a transcription factor, ERG per se does not cause tumorigenesis. Instead, the downstream genes that are activated (or suppressed) by ERG in the human prostate could have contributed to prostate cancer development. Similarly, as a transcription factor, p53 exerts its tumor suppressor function mainly through its downstream transcriptional products, such as p21 and Bax.

The present disclosure utilizes ERG targets, in certain embodiments, to satisfy a long-felt need in the art to provide means to determine prognosis, diagnosis, and/or treatment regimens for cancer, such as for prostate cancer.

BRIEF SUMMARY

The present disclosure is directed to methods and compositions that facilitate prognosis, diagnosis, and/or treatment of cancer. The cancer may be of any kind, but in specific embodiments the cancer is prostate or breast cancer. In some embodiments, however, the cancer is of the lung, brain, liver, skin, kidney, bone, blood, testicle, spleen, colon, ovary, cervix, pituitary gland, thyroid, endometrium, stomach, gall bladder, appendix, and so on.

In particular embodiments of the disclosure, there are methods and compositions that allow determination of an individual's need for one or more particular types of cancer treatment. The needed treatment may or may not be aggressive, depending on the outcome of methods of the disclosure. In particular aspects of the disclosure, it is determined if an individual is in need of a therapeutically effective amount of one or more cancer treatments when a particular result is determined with one or more methods of the disclosure. In specific embodiments, an individual is provided a therapeutically effective amount of one or more cancer treatments when a particular result is determined with one or more methods of the disclosure. In particular cases, the results indicate that patients with Tudor Domain Containing 1 (TDRD1)$^+$ ERG$^-$ prostate tumors (TDRD1 positive, ERG negative) have the best prognosis. These individuals can receive watchful waiting, for example. On the other hand, individuals with TDRD1$^-$ERG$^+$ prostate tumors (TDRD1 negative, ERG positive) have the worst prognosis. These individuals need to be aggressively treated, such as with radical prostatectomy, for example. Individuals with TDRD1$^+$ERG$^+$ prostate tumors (double positive) have the second best prognosis, while individuals with TDRD1$^-$ERG$^-$ prostate tumors (double negative) have the third best prognosis, These two groups of patients receive appropriate treatment based on other criteria, such as Gleason score, for example. In some embodiments, one can treat double positive patients with TDRD1 and/or ERG specific inhibitors or with other agents, for example.

In embodiments of the disclosure, one can identify which tumors need to be aggressively treated and which do not need to be aggressively treated. In specific embodiments, there is a genetically-based test to determine which prostate (or breast) cancers might become more virulent and require aggressive treatment and which tumors may not.

In particular embodiments of the disclosure, the expression of TDRD1 is identified to facilitate prognosis, diagnosis, and/or treatment for a cancer, including at least prostate or breast cancer. In particular embodiments of the disclosure, certain characteristics of the cancer may be determined in addition to identifying the expression level of TDRD1, including identifying the level of one or more other markers and/or determining the stage of the cancer, for example. In some embodiments, the expression level of ERG is similarly determined and/or utilized.

The present disclosure addresses deficiencies in the prior art by identifying TDRD1 as being differentially expressed in human prostate cancer compared to normal human prostate or is differentially expressed in human breast cancer compared to normal human breast. The encoded mRNA species and/or the corresponding encoded protein species have utility, for example, as markers of prostate cancer. Antibodies against the encoded protein species, as well as antisense constructs specific for the mRNA species, have utility for methods of therapeutic treatment of prostate cancer. In addition, the cDNA sequence can be used to design probes and primers for identification of a full length genomic sequence, as well as the promoter sequence for the gene, of use in the design of prostate specific expression vectors of utility in the gene therapy of prostate cancer.

In certain embodiments, the nucleic acid sequence of TDRD1 can be used to design specific oligonucleotide probes and primers. When used in combination with nucleic acid hybridization and amplification procedures, for example, these probes and primers permit the rapid analysis of prostate biopsy core specimens, breast biopsy samples, serum, nipple aspirate (for breast), or blood or urine samples, etc. This will assist medical practitioners in diagnosing and/or prognosticating prostate cancer and/or in determining optimal treatment courses for individuals with prostate tumors of varying malignancy. The same probes and primers also may be used for in situ hybridization or in situ PCR detection and diagnosis of prostate cancer.

In one embodiment of the present disclosure, the isolated nucleic acids of the present disclosure are incorporated into expression vectors and expressed as the encoded proteins or peptides. Such proteins or peptides may, in certain embodiments, be used as antigens for induction of monoclonal or polyclonal antibody production.

One aspect of the present disclosure is, thus, oligonucleotide hybridization probes and primers that hybridize selectively to samples of prostate cancer. The use of probes and primers specific for prostate- or breast-specific nucleic acid sequences, that are differentially expressed in prostate cancer, provides the basis for diagnostic kits useful for distinguishing between normal prostate, prostate organ-confined cancer, and metastatic prostate tumors. Alternatively, the availability of probes and primers that hybridize to one or more TDRD1 or ERG nucleic acids provide the basis for diagnostic kits useful in the detection of prostate cancer. A microassay substrate may be employed in embodiments of the analysis.

In one aspect, the present disclosure encompasses kits for use in detecting prostate or breast cancer cells in a biological sample. Such a kit may comprise one or more pairs of primers for amplifying nucleic acids corresponding to TDRD1 and/or ERG. The kit may further comprise samples of total mRNA derived from tissue of various physiological states, such as normal, BPH, confined tumor and metastatically progressive tumor, for example, to be used as controls or standards. The kit also may comprise buffers, nucleotide bases, and other compositions to be used in hybridization and/or amplification reactions. Each solution or composition may be contained in a vial or bottle and all vials held in close confinement in a box for commercial sale. Another embodiment of the present disclosure encompasses a kit for use in detecting prostate cancer or breast cancer cells in a biological sample comprising oligonucleotide probes effective to bind with high affinity to nucleic acids corresponding to TDRD1 or ERG mRNA in a Northern blot assay and containers for each of these probes. In a further embodiment, the disclosure encompasses a kit for use in detecting prostate cancer or breast cancer cells in a biological sample comprising antibodies specific for proteins encoded by nucleic acids corresponding to TDRD1 or ERG, respectively.

In one aspect, the present disclosure encompasses methods for treating prostate cancer patients by administration of effective amounts of antibodies specific for TDRD1, or by administration of effective amounts of vectors producing antisense messenger RNAs that bind to nucleic acids corresponding to TDRD1, thereby inhibiting expression of the protein products of a prostate specific gene that is overexpressed in prostate cancer. Antisense nucleic acid molecules also may be provided as RNAs, as some stable forms of RNA with a long half-life that may be administered directly without the use of a vector are now known in the art. In addition, DNA constructs may be delivered to cells by liposomes, receptor mediated transfection and other methods known in the art. Delivery of the present agents, by any means known in the art would be encompassed by the present disclosure.

Embodiments of the method further comprise methods for detecting prostate cancer or breast cancer cells in biological samples, using hybridization primers and probes designed to specifically hybridize to nucleic acids corresponding to TDRD1 or ERG. This method further comprises measuring the amounts of nucleic acid amplification products formed when primers selected from the designated sequences are used.

The disclosure further comprises the prognosis and/or diagnosis of prostate or breast cancer by measuring the amounts of nucleic acid amplification products. The disclosure comprises methods of treating individuals with prostate cancer by providing effective amounts of antibodies and/or antisense DNA molecules that bind to the products of the above mentioned isolated nucleic acids. The disclosure further comprises kits for performing the above-mentioned procedures, containing antibodies, amplification primers and/or hybridization probes.

The present disclosure further comprises production of antibodies specific for proteins or peptides encoded by nucleic acids corresponding to TDRD1. In some cases, ERG antibodies are employed. In at least some cases, the use of those antibodies for diagnostic applications in detecting or prognosticating prostate or breast cancer. The disclosure further comprises therapeutic treatment of prostate or breast cancer by administration of effective doses of inhibitors specific for the aforementioned encoded proteins.

In particular embodiments of the disclosure, TDRD1 is a novel cancer biomarker. It can be used for diagnosis and/or prognosis of prostate and other tumors, such as breast. In some cases, it is a therapeutic target for treatment of prostate or breast cancer. In specific embodiments, the cancer is TDRD1 positive or TDRD1 negative. In specific embodiments, the cancer is ERG positive or ERG negative.

In some embodiments, there is a method of determining a cancer diagnosis, prognosis, and/or treatment regimen for an individual suspected of having cancer (such as prostate cancer or breast cancer) or known to have cancer, comprising the step of assaying the level of expression of TDRD1 from a sample from the individual. An individual may be suspected of having a particular cancer because they have one or more risk factors (such as have an enlarged prostate, have inflammation of the prostate gland, are a smoker, are obese, and/or are over the age of 45, 50, 55, 60, or 65, for example), have a personal history, and/or have a family history. In particular aspects, when the level of TDRD1 is determined, the individual is provided a therapeutically effective amount of a suitable cancer therapy, such as watchful waiting, surgery, radiation, hormone therapy, chemotherapy, biologic therapy, or a combination thereof. The sample may be of any kind, but in specific embodiments, the sample is blood, biopsy, or urine or nipple aspirate (for breast). In cases wherein the cancer is breast cancer, the breast cancer may be HER2+. An assaying step may be further defined as comparing the level of expression of TDRD1 to a standard.

In particular aspects of methods of the disclosure, at least certain methods further comprise the step of assaying the level of expression of ERG from a sample from the individual. The sample for assaying the TDRD1 level and the sample for assaying the ERG level may be the same sample or may be a different sample.

In particular embodiments, when the individual is TDRD1-positive and ERG-negative, the individual has a good prognosis, and a certain action may or may not be taken. In certain embodiments, when the individual is TDRD1-negative and ERG-negative, the individual has a poor prognosis and a certain action may be taken.

In some aspects of the disclosure, a method further comprises the step of providing a therapeutically effective amount of a suitable cancer therapy In some embodiments, there is a method of treating an individual for cancer, comprising the step of providing to the individual a therapeutically effective amount of therapy for the cancer when a sample from the individual indicates there is overexpression of TDRD1, ERG, or both in cancer cells in the sample.

In some embodiments, there is a method of determining a cancer diagnosis, prognosis, and/or treatment regimen for an individual suspected of having cancer (such as prostate cancer or breast cancer) or known to have cancer, comprising the step of assaying a sample from the individual for a variant of TDRD1 (in addition to or instead of assaying for the wild-type TDRD1), such as one that has one or more mutations compared to wild-type full-length TDRD1. The TDRD1 variant may have 1, 2, 3, 4, 5, 6, 7, 8, 9, 10, or more amino acid alterations compared to wild-type TDRD1. The TDRD1 variant may comprise an insertion and/or deletion compared to wild-type TDRD1. An insertion or deletion may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more amino acids. The insertion or deletion may be anywhere in the TDRD1 sequence, including the N-terminus, C-terminus, or both.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present disclosure, reference is now made to the following descriptions taken in conjunction with the accompanying drawing, in which:

FIG. 1A shows oncoprints of ERG and TDRD1 in 131 primary prostate tumors (Cancer Cell 2010. 18:11-22); FIG. 1B shows ERG and TDRD1 expression in 18 human PCa samples;

DETAILED DESCRIPTION

Figure 1:
FIG. 1 shows co-expression of ERG and TDRD1 in primary prostate tumors.
Figure 1:
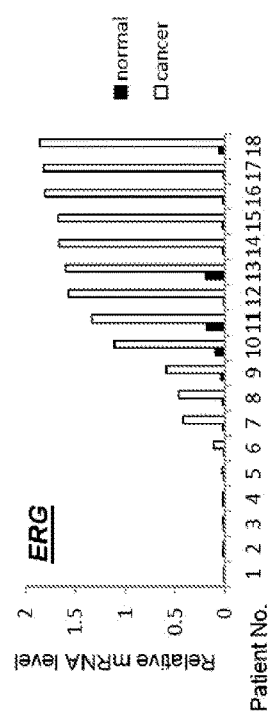
Figure 1:
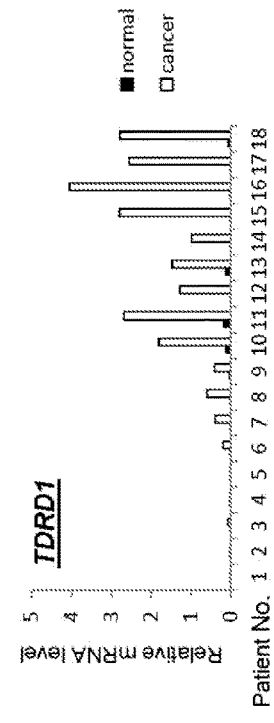

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the disclosure may "consist essentially of" or "consist of" one or more sequences of the disclosure, for example. Some embodiments of the disclosure may consist of or consist essentially of one or more elements, method steps, and/or methods of the disclosure. It is contemplated that any method or composition described herein can be implemented with respect to any other method or composition described herein. Embodiments discussed in the context of methods and/or compositions of the disclosure may be employed with respect to any other method or composition described herein. Thus, an embodiment pertaining to one method or composition may be applied to other methods and compositions of the disclosure as well.

I. General Embodiments

Oncogenic ERG is expressed in ~50% of prostate tumors and is believed to be the driver of prostate tumorigenesis. ERG is being intensively studied as therapeutic target for prostate cancer. However, it is considered that ERG alone does not have prognostic value based on multiple previous studies. Disclosed herein are prognostic, diagnostic, and/or therapeutic embodiments for analysis of expression of downstream targets of ERG. In specific embodiments, there are prognostic, diagnostic, and/or therapeutic methods for Tudor Domain Containing 1 (TDRD1). In specific aspects, the level of TDRD1 is determined as a sole factor or among multiple factors for a prognosis, diagnosis, and/or treatment for cancer, such as prostate cancer or breast cancer. In at least some cases, the level of expression of TDRD1 is useful to help determine a treatment course for cancer, including prostate or breast cancer (which may be HER2-positive). Thus, without the analysis of the expression of TDRD1, the appropriate treatment course would be unknown and without such analysis may be inappropriate for the individual. The treatment to be employed may or may not be aggressive, depending on the outcome of the analysis of TDRD1 expression. Aggressive treatment includes radical prostatectomy, which is a surgical procedure to remove the prostate and surrounding tissues. In specific embodiments, when the level of TDRD1 is overexpressed in a sample from an individual, the individual may have a good prognosis for cancers, such as prostate and breast cancer. In some embodiments of methods disclosed herein, the cancer is ERG-positive, whereas in other embodiments the cancer is ERG-negative.

In some embodiments, there is a treatment regimen for an individual with cancer that depends on analysis of expression of TDRD1 to determine which treatment regimen is suitable. Thus, in particular aspects, an individual is provided a particular cancer treatment when the expression level of TDRD1 is overexpressed or a particular cancer treatment when the expression level of TDRD1 is not detectable or at very low levels.

In some diagnosis embodiments, TDRD1 expression is assayed in the absence of assaying ERG expression. In some prognosis embodiments, both TDRD1 expression and EGR expression are assayed.

In certain embodiments of the disclosure, when a sample from an individual indicates that cancer cells are TDRD1-negative and ERG-positive, the individual will more likely have metastatic cancer and/or cancer that has a poor prognosis for the individual; in particular embodiments, the individual will require aggressive treatment. In certain embodiments of the disclosure, when a sample from an individual indicates that cancer cells are TDRD1-positive and ERG-negative, the individual will more likely have a good prognosis for the individual; in particular embodiments, the individual will require watchful waiting and no imminent treatment, for example.

Any sample that is suitable may be obtained from an individual, so long as the sample comprises one or more cancer cells or is suspected of comprising one or more cancer cells. The sample may be obtained from the individual and the assay may be performed by the individual by the same or different individuals or organizations. The sample may be stored under suitable conditions prior to analysis. The sample may be transported under suitable conditions prior to analysis. In some embodiments, the sample comprises biopsy of the respective organ or tissue (such as prostate or breast), although in specific embodiments the sample may comprise blood, urine, nipple aspirate, and so forth.

Embodiments may include the collection of a sample of prostate tissue. Methods may also include determining whether prostate cancer is aggressive. In some aspects, methods may include grading of the cancer to determine its stage and to provide information on how aggressive the cancer is. The most routinely used scale to evaluate the grade of prostate cancer cells is the Gleason score, wherein scores for prostate cancer can range from 2 (nonaggressive cancer) to 10 (very aggressive cancer). One may determining if the cancer is spread and, if so, how far the cancer has spread. Stages include the following: Stage I is very early cancer confined to a small area of the prostate; microscopically, the cancer cells aren't considered aggressive; Stage II is still small, but may be considered aggressive when cancer cells are viewed microscopically, or, the cancer may be larger and may have grown to involve both sides of the prostate gland; in Stage III, the cancer has spread beyond the prostate to the seminal vesicles or other nearby tissues; and in Stage IV, the cancer has metastasized to invade nearby organs, such as the bladder, or spread to lymph nodes, bones, lungs or other organs.

II. TDRD1 AND ERG

In some embodiments, TDRD1 expression level is determined and utilized for prognosis, diagnosis, and/or treatment for cancer. The skilled artisan recognizes that TDRD1 may alternatively be called CT41.1, Cancer/Testis Antigen 41.1, or Tudor Domain Containing Protein 1, for example. The skilled artisan recognizes that the TDRD1 sequence may be found at least at National Center for Biotechnology Information's GenBank® website, in particular at NM_198795 for the nucleic acid sequence and NP_942090 for the protein sequence.

In some embodiments, expression level of TDRD1 is determined by its nucleic acid level, although in some cases the expression level of TDRD1 is determined by its protein level, or both. In specific cases, an antibody, such as a monoclonal antibody, is employed for assaying samples for presence of TDRD1. In embodiments of the disclosure, there is successful development of a mouse monoclonal antibody that specifically recognizes TDRD1 protein in a variety of assays, including Western blot, Immunohistochemistry, Immunofluorescence staining, and Immunoprecipitation.

In particular embodiments, ERG expression level is determined and utilized for prognosis, diagnosis, and/or treatment for cancer. The skilled artisan recognizes that an exemplary ERG sequence may be found at least at National Center for Biotechnology Information's GenBank® website, in particular at AY204741 for the nucleic acid sequence and AAP41719 for the protein sequence.

In some embodiments, expression level of ERG is determined by its nucleic acid level, although in some cases the expression level of ERG is determined by its protein level, or both. In specific cases, an antibody, such as a monoclonal antibody, is employed for assaying samples for presence of ERG. In embodiments of the disclosure, there is successful development of a mouse monoclonal antibody that specifically recognizes ERG protein in a variety of assays, including Western blot, Immunohistochemistry, Immunofluorescence staining, and Immunoprecipitation.

III. Treatment Regimen for Cancer

In some embodiments of the disclosure, an individual is treated with a particular treatment upon determination of the expression level of TDRD1 or TDRD1 and ERG, for example. In specific embodiments, the treatment is tailored for the individual based on the outcome of analysis of the expression level of TDRD1 or TDRD1 and ERG. In particular embodiments, without such analysis, an inappropriate treatment regimen may be given to the individual, such as one that is not suitable because it is excessive for the type of cancer the individual has or one that is not suitable because it is insufficient for the type of cancer the individual has. The therapy may include watchful waiting; chemotherapy; hormone therapy (Luteinizing hormone-releasing hormone, such as leuprolide, goserelin, and buserelin; anti-androgens, such as enzalutamide, flutamide, and nilutamide; drugs that can prevent the adrenal glands from making androgens, such as ketoconazole and aminoglutethimide; and/or estrogens); gene therapy; radiation; surgery (to remove part or all of the prostate); biologic therapy; cryosurgery; high-intensity focused ultrasound; proton beam radiation therapy; freezing prostate tissue; heating prostate tissue using ultrasound; or a combination thereof.

Exemplary prostate cancer drugs include Abiraterone Acetate; Cabazitaxel; Degarelix; Docetaxel; Enzalutamide; Jevtana (Cabazitaxel); Leuprolide Acetate; Lupron (Leuprolide Acetate); Lupron Depot (Leuprolide Acetate); Lupron Depot-3 Month (Leuprolide Acetate); Lupron Depot-4 Month (Leuprolide Acetate); Lupron Depot-Ped (Leuprolide Acetate); Prednisone; Provenge (Sipuleucel-T); Radium 223 Dichloride; Sipuleucel-T; Taxotere (Docetaxel); Viadur (Leuprolide Acetate); Xofigo (Radium 223 Dichloride); Xtandi (Enzalutamide); Zytiga (Abiraterone Acetate), or a combination thereof.

In some embodiments, the individual is provided a therapeutic agent that targets the TDRD1 mRNA or protein, particularly when it is determined that the individual has cancer that is TDRD1-positive. In specific embodiments, a nucleic acid is employed that TDRD1 siRNA (h), shRNA and Lentiviral Particle Gene Silencers (Santa Cruz Biotechnology; Santa Cruz, Calif.) or shRNA, for example. In specific embodiments, small chemical compounds can be used to specifically inhibit TDRD1 protein.

In specific embodiments, the individual is provided a therapeutic agent that targets the ERG mRNA or protein, particularly when it is determined that the individual has cancer that is ERG-positive. In specific embodiments, a nucleic acid is employed that ERG siRNA (h), shRNA and Lentiviral Particle Gene Silencers (Santa Cruz Biotechnology; Santa Cruz, Calif.) or shRNA, for example. In specific embodiments, small chemical compounds can be used to specifically inhibit ERG protein.

IV. Additional Methods for Diagnosis of Cancer

In some embodiments, one or more other methods of prognosis, diagnosis, and/or treatment of cancer may be employed in conjunction with the respective methods of the disclosure. For example, for prostate cancer, one may also utilize a Digital Rectal Exam (DRE); prostate-specific antigen (PSA) test and/or a transrectal. In some cases where the presence of prostate cancer is already known or suspected, one may include imaging tests, such as bone scan; ultrasound; Computerized tomography (CT) scan; Magnetic resonance imaging (MRI); radiation therapy (external beam radiation and/or brachytherapy); or a combination thereof.

V. Nucleic Acid Detection

In certain embodiments of the disclosure, the level of one or more gene products is determined. In specific cases, the gene product is TDRD1. The level may be of a nucleic acid, although in other embodiments the level is detected of a protein. Certain nucleic acids also have utility as probes or primers for embodiments involving nucleic acid hybridization.

A. Hybridization

The use of a probe or primer of between 13 and 100 nucleotides, preferably between 17 and 100 nucleotides in length, or in some aspects of the disclosure up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the disclosure may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present disclosure in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present disclosure are disclosed in U.S. Pat. Nos. 5,849,481, 5,849,486 and 5,851,772. The relevant portions of these and other references identified in this section of the Specification are incorporated herein by reference.

B. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to TDRD1 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present disclosure are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present disclosure. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present disclosure (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present disclosure.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

C. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present disclosure, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present disclosure.

Other methods of nucleic acid detection that may be used in the practice of the instant disclosure are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

D. Other Assays

Other methods for genetic screening may be used within the scope of the present disclosure, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present disclosure are disclosed in U.S. Pat. Nos. 5,849,483, 5,851,770, 5,866,337, 5,925,525 and 5,928,870, each of which is incorporated herein by reference in its entirety.

VI. Immunodetection Methods

The following description of examples of immunodetection methods applies to any protein or peptide, including TDRD1 and/or ERG, although for the sake of brevity TDRD1 is described.

In still further embodiments, the present disclosure concerns immunodetection methods for recognizing TDRD1 in a sample. TDRD1 antibodies of any kind may be employed to detect wild-type and/or mutant TDRD1 proteins, polypeptides and/or peptides. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

In general, the immunobinding methods include obtaining a sample suspected of containing TDRD1 protein, polypeptide and/or peptide, and contacting the sample with a TDRD1 antibody under conditions effective to allow the formation of immunocomplexes.

The immunobinding methods include methods for detecting and optionally quantifying the amount of a wild-type TDRD1 protein reactive component in a sample and the detection and optionally quantification of any immune complexes formed during the binding process. Here, one would obtain a sample suspected of containing a wild-type TDRD1 protein and/or peptide, and contact the sample with an antibody against wild-type TDRD1, and then detect and quantify the amount of immune complexes formed under the specific conditions.

In terms of antigen detection, the biological sample analyzed may be any sample that is suspected of containing a wild-type TDRD1 protein-specific antigen, such as a tissue section or specimen, a homogenized tissue extract, a cell, separated and/or purified forms of any of the above wild-type protein-containing compositions, or even any biological fluid that comes into contact with the tissue, including blood and/or serum. Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any TDRD1 protein antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

In the clinical diagnosis and/or monitoring of patients with cancer, the detection of an alteration in the levels of TDRD1, in comparison to the levels in a corresponding biological sample from a normal subject is indicative of a patient with cancer, such as prostate or breast cancer. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive.

A. ELISAs

As detailed above, immunoassays, in their most simple and/or direct sense, are binding assays. Certain preferred immunoassays are the various types of enzyme linked immunosorbent assays (ELISA) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the anti-TDRD1 antibodies of the disclosure are immobilized onto a selected surface exhibiting protein affinity, such as a well in a polystyrene microtiter plate. Then, a test composition suspected of containing the wild-type TDRD1 protein antigen, such as a clinical sample, is added to the wells. After binding and/or washing to remove non-specifically bound immune complexes, the bound wild-type TDRD1 protein antigen may be detected. Detection is generally achieved by the addition of another anti-TDRD1 antibody that is linked to a detectable label. This type of ELISA is a simple "sandwich ELISA". Detection may also be achieved by the addition of a second anti-TDRD1 antibody, followed by the addition of a third antibody that has binding affinity for the second antibody, with the third antibody being linked to a detectable label.

In another exemplary ELISA, the samples suspected of containing the wild-type TDRD1 protein antigen are immobilized onto the well surface and/or then contacted with the anti-TDRD1 antibodies of the disclosure. After binding and/or washing to remove non-specifically bound immune complexes, the bound anti-TDRD1 antibodies are detected. Where the initial anti-TDRD1 antibodies are linked to a detectable label, the immune complexes may be detected directly. Again, the immune complexes may be detected using a second antibody that has binding affinity for the first anti-TDRD1 antibody, with the second antibody being linked to a detectable label.

Another ELISA in which the wild-type TDRD1 proteins, polypeptides and/or peptides are immobilized, involves the use of antibody competition in the detection. In this ELISA, labeled antibodies against wild-type protein are added to the wells, allowed to bind, and/or detected by means of their label. The amount of wild-type TDRD1 protein antigen in an unknown sample is then determined by mixing the sample with the labeled antibodies against wild-type TDRD1 before and/or during incubation with coated wells. The presence of wild-type TDRD1 protein in the sample acts to reduce the amount of antibody against wild-type TDRD1 protein available for binding to the well and thus reduces the ultimate signal. This is also appropriate for detecting antibodies against wild-type TDRD1 protein in an unknown sample, where the unlabeled antibodies bind to the antigen-coated wells and also reduces the amount of antigen available to bind the labeled antibodies.

Irrespective of the format employed, ELISA have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISA, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Immunohistochemistry

TDRD1 antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

C. Immunoelectron Microscopy

TDRD1 antibodies may also be used in conjunction with electron microscopy to identify intracellular tissue components. Briefly, and electron-dense label is conjugated directly or indirectly to the anti-TDRD1 antibody. Examples of electron-dense labels according to the disclosure are ferritin and gold. The electron-dense label absorbs electrons and can be visualized by the electron microscope.

VII. Kits

Any of the compositions described herein may be comprised in a kit. In a non-limiting example, one or more agents that determine expression level of TDRD1 or ERG may be comprised in a kit, and/or one or more agents that provide therapy following determination of expression level of TDRD1 or ERG may be comprised in a kit. Exemplary agents include oligonucleotides specific for TDRD1 or ERG, respectively, buffers, deoxyribonucleotides, salts, and so forth. Also included may be one or more prostate cancer or breast cancer therapies. Antibodies that detect TDRD1 or ERG may be included in the kit.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the agent(s), and any other reagent containers in close confinement for commercial sale. Such containers may include injection or blow-molded plastic containers into which the desired vials are retained. However, the components of the kit may be provided as dried powder(s). When reagents and/or components are provided as a dry powder, the powder can be reconstituted by the addition of a suitable solvent. It is envisioned that the solvent may also be provided in another container means.

In certain embodiments, one or more therapies for prostate or breast cancer other than those of the present disclosure are provided in the kit.

VIII. Examples

The following examples are included to demonstrate some embodiments of the disclosure. It should be appreciated by those of skill in the art that the techniques disclosed in the examples which follow represent techniques discovered by the inventor to function well in the practice of the disclosure, and thus can be considered to constitute some modes for its practice. However, those of skill in the art should, in light of the present disclosure, appreciate that many changes can be made in the specific embodiments which are disclosed and still obtain a like or similar result without departing from the spirit and scope of the disclosure.

EXAMPLE 1

General Embodiments

In embodiments of the disclosure, based on unbiased bioinformatics analysis of human prostate cancer gene expression data sets, the inventors have identified a novel gene, TDRD1, that is useful as a diagnostic/prognostic marker for prostate cancer. Briefly, TDRD1 mRNA is not expressed in normal human prostate tissues. However, it is expressed in 68% of primary human prostate tumors (n=131), supporting its role as a diagnostic marker. More importantly, TDRD1-positive prostate cancer patients showed longer disease-free survival (n=131, logrank test p-value: 0.0392), supporting its prognostic value. Finally, TDRD1 protein contained drug-targetable functional domains, suggesting its role a therapeutic target for prostate cancer.

In a search for genes that are regulated by ERG in human prostate tumors and might have contributed to tumorigenesis, datasets of genomic profiling of human prostate cancer (Cancer Cell 2010. 18:11-22) (based on MSKCC Prostate Oncogene Project that concerned transcriptomes in 150 prostate tumors (131 primaries and 19 metastases)) were analyzed. In particular, the mRNA expression dataset was split based on ERG expression. Twenty-two genes were found to be significantly increased, while only one gene was decreased, in ERG positive tumors. Among them, TDRD1 is the most significantly increased gene in ERG positive tumors.

TDRD1 is not expressed in normal prostate. Among 131 primary prostate tumors, TDRD1 is over-expressed in 68% of samples, while ERG is overexpressed in 48% of samples. Expression of ERG and TDRD1 is strongly correlated in this cohort (odds Ratio=43.571429, p=0). Next, to determine if TDRD1 has prognostic value, data were retrieved and analyzed in the cBio Cancer Genomics Portal (http://www.cbioportal.org/). Strikingly, in this cohort, the log-rank test indicates that the difference in disease free survival between TDRD1-positive and TDRD1-negative patients was significantly (p=0.0392), with TDRD1 expression being a good prognostic marker. In contrast, no difference in disease-free survival was found between ERG-positive and ERG-negative patients (p=0.946799). Similarly, none of other genes over-expressed in prostate cancer such as EZH2 or AMACR have prognostic value. This result indicates that TDRD1 expression is a good prognostic marker for prostate tumors. Moreover, TDRD1 expression is independent of Gleason score and therefore provides a unique molecular marker for prostate cancer prognosis.

Next, the inventors considered that ERG might directly regulate TDRD1 expression in prostate tumors. Among all the commonly used prostate cancer cell lines, VCaP is the only cell line that harbors a TMPRSS2-ERG translocation and expresses ERG mRNA. Meanwhile, VCaP is also the only cell line that express TDRD1, in support of their correlated expression observed in human prostate tumors. ChIP-seq analysis of ERG genomic binding sites in VCaP cells was previously performed (Cancer Cell 2010, 17:443-54). The data were retrieved, analyzed, and ERG was found to directly bind to TDRD1 promoter, suggesting that ERG directly regulates the expression of TDRD1 in human prostate tumors.

Finally, in normal tissues, TDRD1 is exclusively expressed in germ cells: in testis in male and in oocyte in female. Because germ cells are ultimate stem cells that are immortal, TDRD1 confers the "sternness" properties to the prostate luminal cells and contribute to tumorigenesis, in specific embodiments of the disclosure.

In summary, the inventors determined that TDRD1, a germ cell-specific gene, is over-expressed in 68% of primary prostate tumors. TDRD1 expression in prostate tumors is probably induced by both ERG-dependent and ERG-independent manners. In embodiments of the disclosure, TDRD1 expression defines a subtype of prostate cancer with good prognosis. One can use routine methods in the art to develop a mouse monoclonal antibody against TDRD1. In specific embodiments, TDRD1 immunohistochemistry staining on human prostate tumor biopsy has useful prognostic value.

EXAMPLE 2

Co-Expression of ERG and TDRD1 in Primary Prostate Tumors

FIG. 1. Oncoprints of ERG and TDRD1 in 131 primary prostate tumors. Individual genes (ERG and TDRD1) are represented as rows, while individual patients are represented as columns. Among 131 primary prostate tumors, TDRD1 mRNA is overexpressed in 68% of samples, and ERG mRNA levels are altered in 48% of samples. Expression of ERG and TDRD1 is strongly correlated, Odds Ratio=43.571429 and p-value=0. This result is based on Memorial Sloan-Kettering Cancer Center (MSKCC) Prostate Oncogene Project, which includes 181 primary, 37 metastatic prostate cancer samples, 12 prostate cancer cell lines and xenografts. (Cancer Cell 2010. 18:11-22).

EXAMPLE 3

TDRD1: A Potential Prognostic Marker for Primary PC

Figure 2:
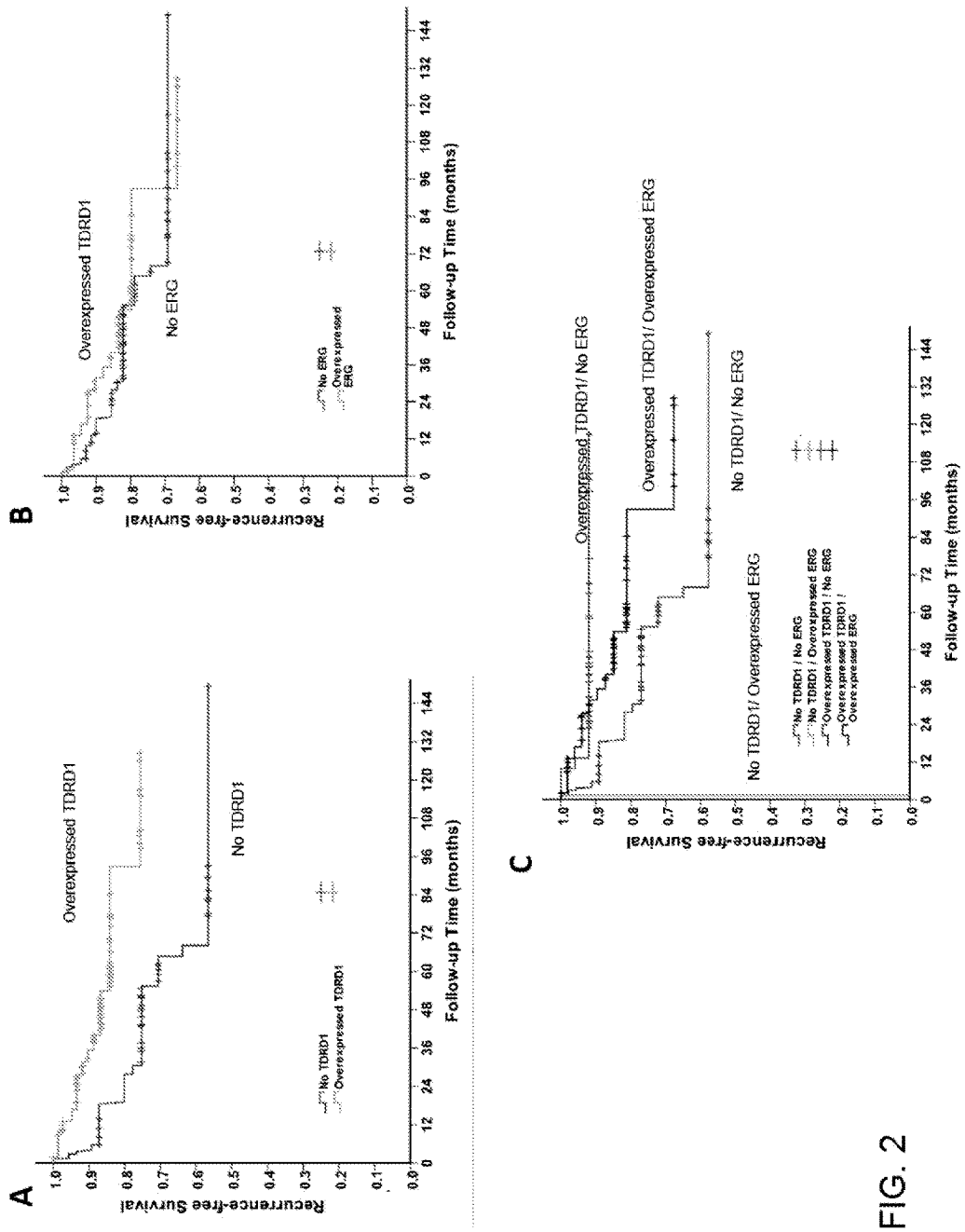
FIG. 2A-2C shows that TDRD1 (and in combination with ERG) is a useful prognostic marker for primary prostate cancer.

FIG. 2. TDRD1 as a potential prognostic marker for prostate cancer. Among 131 primary prostate cancer patients, disease free survival rates were shown, logrank test P-Value: 0.0392 for TDRD1 and 0.946799 for ERG. The data indicate that TDRD1, but not ERG, is a good prognostic marker. None of other genes over-expressed in prostate cancer, such as EZH2 or AMACR, have prognostic value. Data were retrieved and analyzed in The cBio Cancer Genomics Portal (http://www.cbioportal.org/).

EXAMPLE 4

Erg Directly Binds to TDRD1 Promoter

Figure 3:
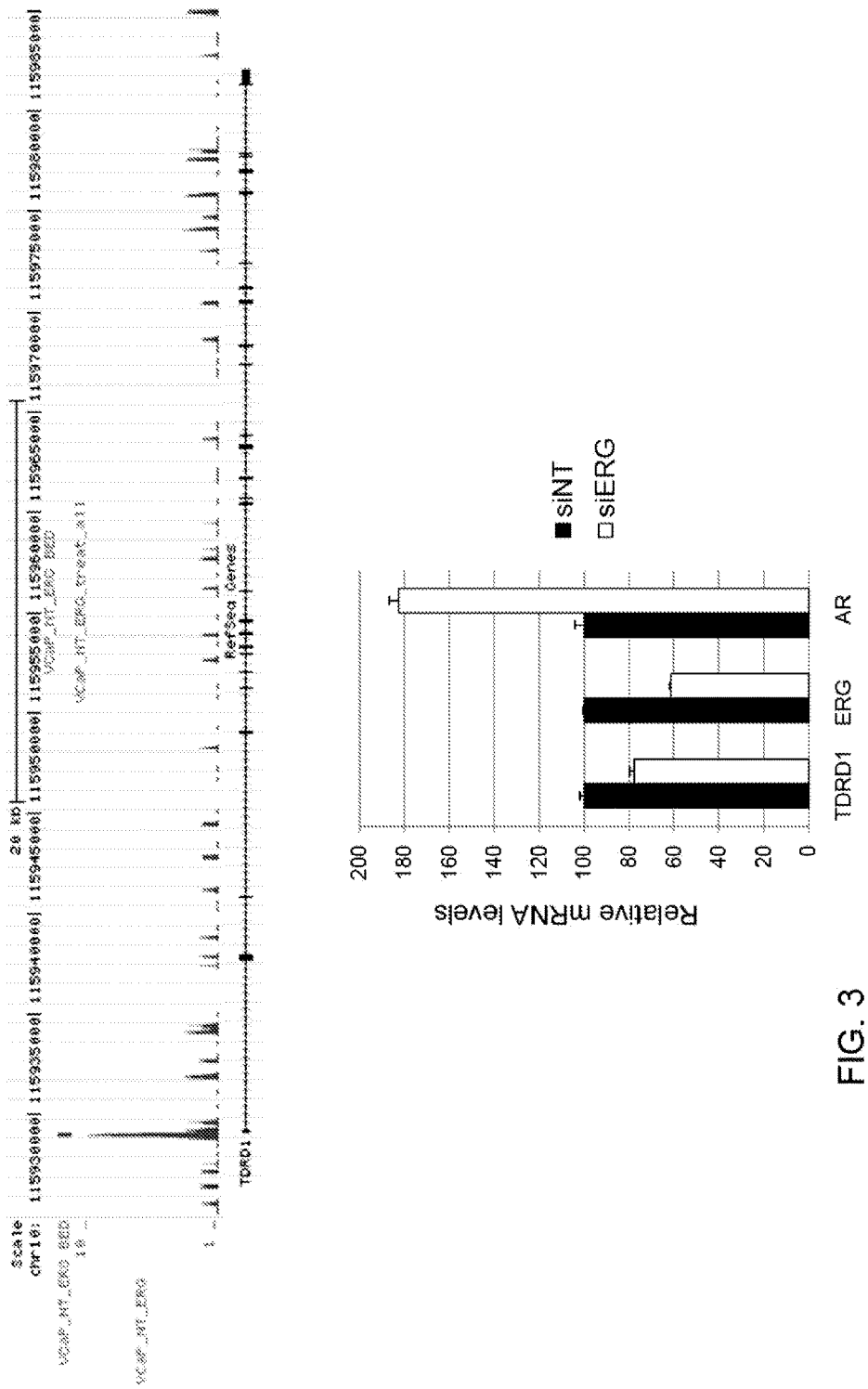
FIG. 3 shows that ERG directly binds to TDRD1 promoter in prostate cancer VCaP cells and knockdown of ERG reduced the TDRD1 mRNA expression.

FIG. 3. Evidence that ERG directly regulates TDRD1 expression in prostate tumors. Among the commonly used prostate cancer cell lines, VCaP is the only cell line that contains TMPRSS2-ERG fusion and expresses ERG mRNA. Interestingly, VCaP is also the only cell line that express TDRD1, in support of their correlated expression observed in human prostate tumors. ChIP-seq analysis of ERG genomic binding sites in VCaP cells was previously performed in Chinnaiyan's laboratory (Cancer Cell 2010, 17:443-54). The data were retrieved, analyzed, and ERG was found to directly binds to TDRD1 promoter, suggesting that ERG directly regulates the expression of TDRD1 at transcription level. Moreover, knockdown of ERG in VCaP cells reduced the TDRD1 mRNA level.

EXAMPLE 5

Exclusive Expression of TDRD1 in Mouse Testis and Ovary

Figure 4:
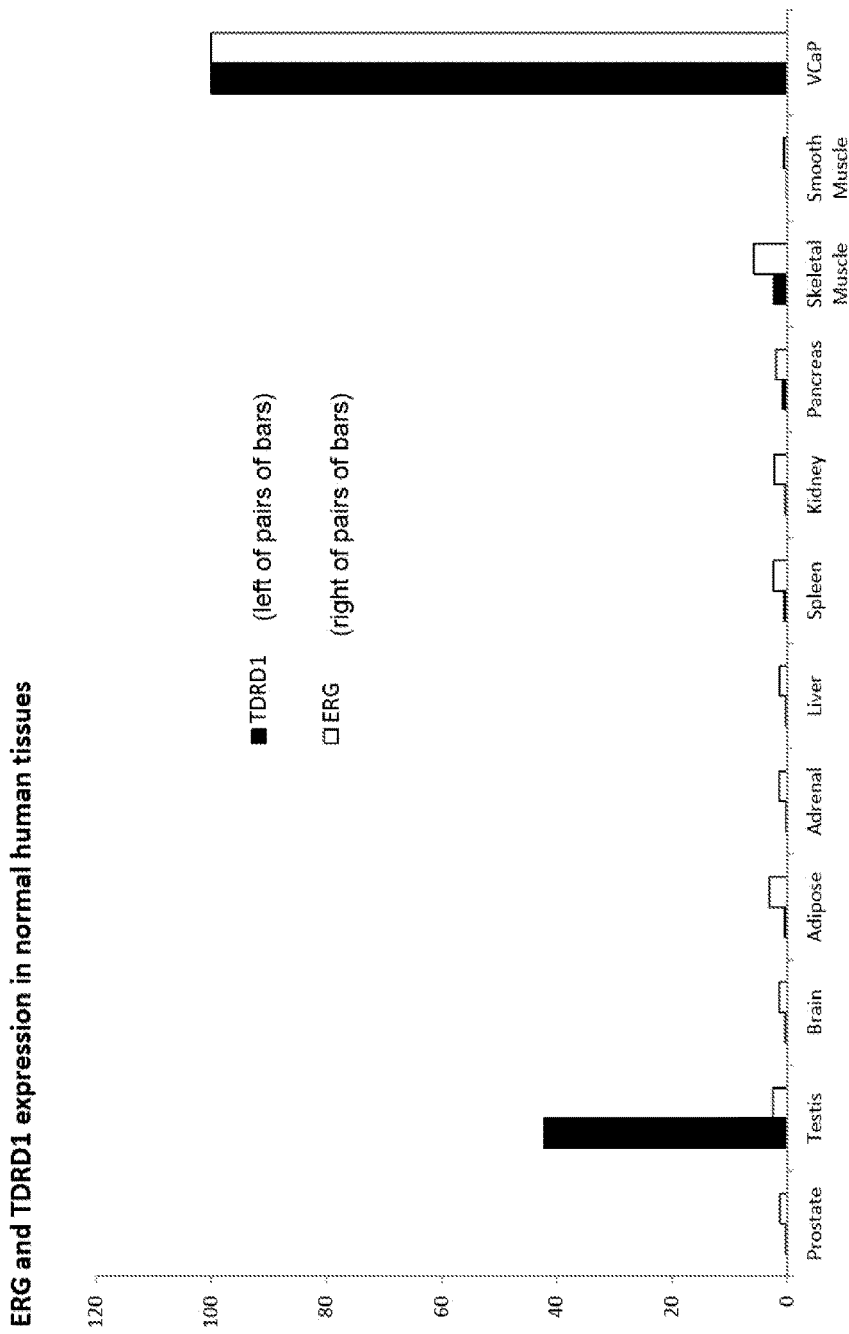
FIG. 4 demonstrates that there is exclusive expression of TDRD1 in human testis in the male.

FIG. 4. TDRD1 is exclusively expressed in human testis in male. Germ cells are ultimate stem cells that are immortal. Thus, in specific embodiments, TDRD1 confers the "stemness" properties to the prostate luminal cells and contribute to tumorigenesis.

EXAMPLE 6

Cloning of Full-Length TDRD1 cDNA from VCaP Cells

Microarray analysis suggests TDRD1 mRNA is expressed in 68% of human primary prostate tumors. To verify this, the full length TDRD1 cDNA was cloned from prostate cancer cells. VCaP cell total RNA was first reverse transcribed, and PCR was performed to amplify the full length cDNA. PCR product was subsequently cloned into the mammalian expression vector pCMVS. cDNA clones were verified by DNA sequencing.

Conclusion: (1) By RT-PCR, the inventors successfully cloned the full length TDRD1 cDNA from VCaP cells, which encodes 1189 amino acids, identical to NP_942090.1. (2) The inventors also cloned a TDRD1 cDNA variant from VCaP cells, which lacks the last 10 amino acids.

EXAMPLE 7

TDRD1 Protein is Expressed in VCaP Cells

TDRD1 mRNA is expressed in prostate cancer. To determine if TDRD1 protein is expressed in prostate cancer cells, the inventors have generated a TDRD1-specific mouse monoclonal antibody. GST-TDRD1(23-248) fusion protein was expressed and purified from bacteria, and was used to immunize five mice. After two rounds of immunization, the mouse antisera were obtained. Antibody-producing B cells were fused with myeloma cells to generate hybridomas. Out of eight clones of hybridomas that were selected, clone #1277 shows high specificity and sensitivity towards human TDRD1 protein.

Figure 5:
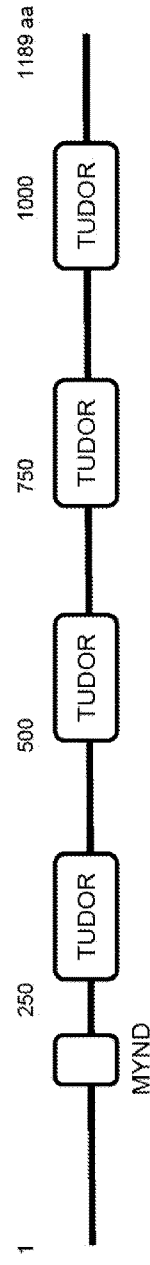
FIG. 5 shows the primary structure of human TDRD1 protein (A); purified GST-TDRD1(23-248) protein used for immunization of mice to generate antibody (B); and specific recognition of full length TDRD1 protein (130 kDa) by a home-made mouse monoclonal antibody (C)
Figure 5:
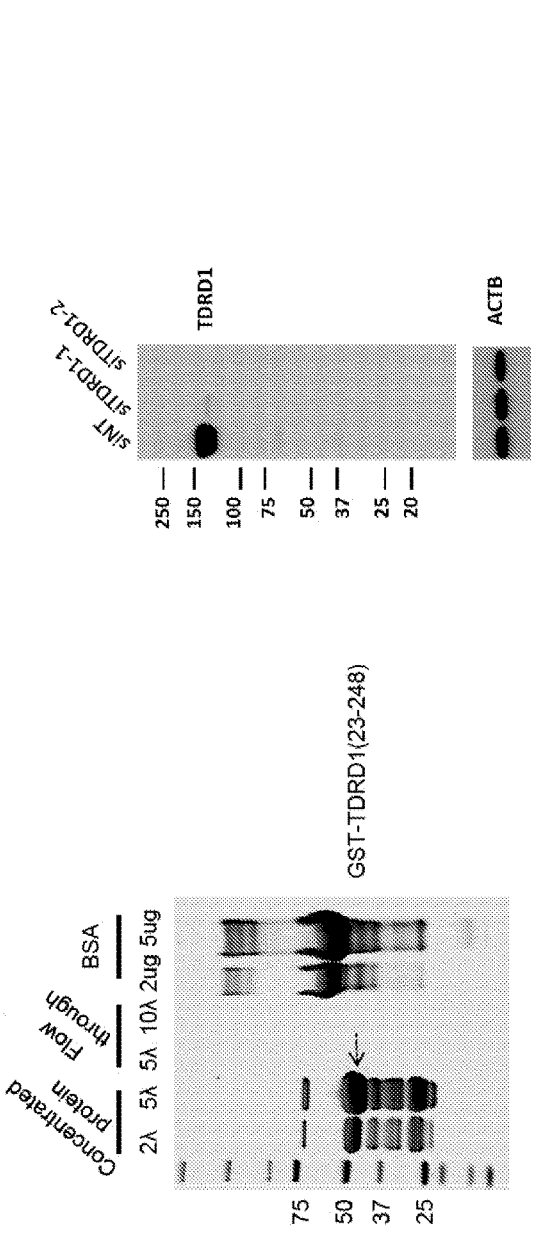
Figure 6:
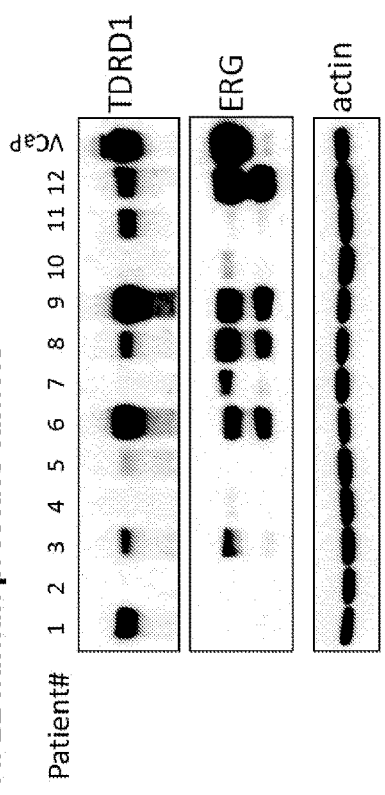
FIG. 6 shows that TDRD1 and ERG protein is expressed in the majority of human prostate tumor samples (A); but not in normal human prostate tissues (B).
Figure 6:
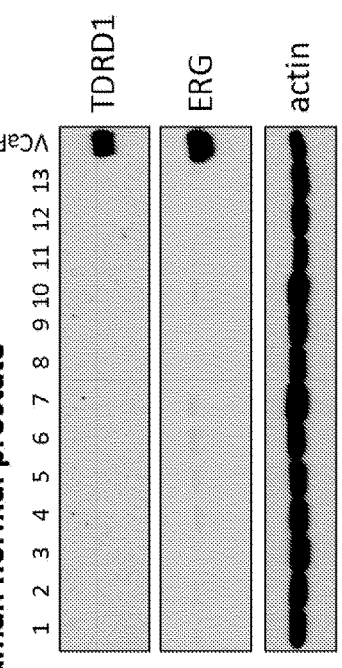
Figure 9:
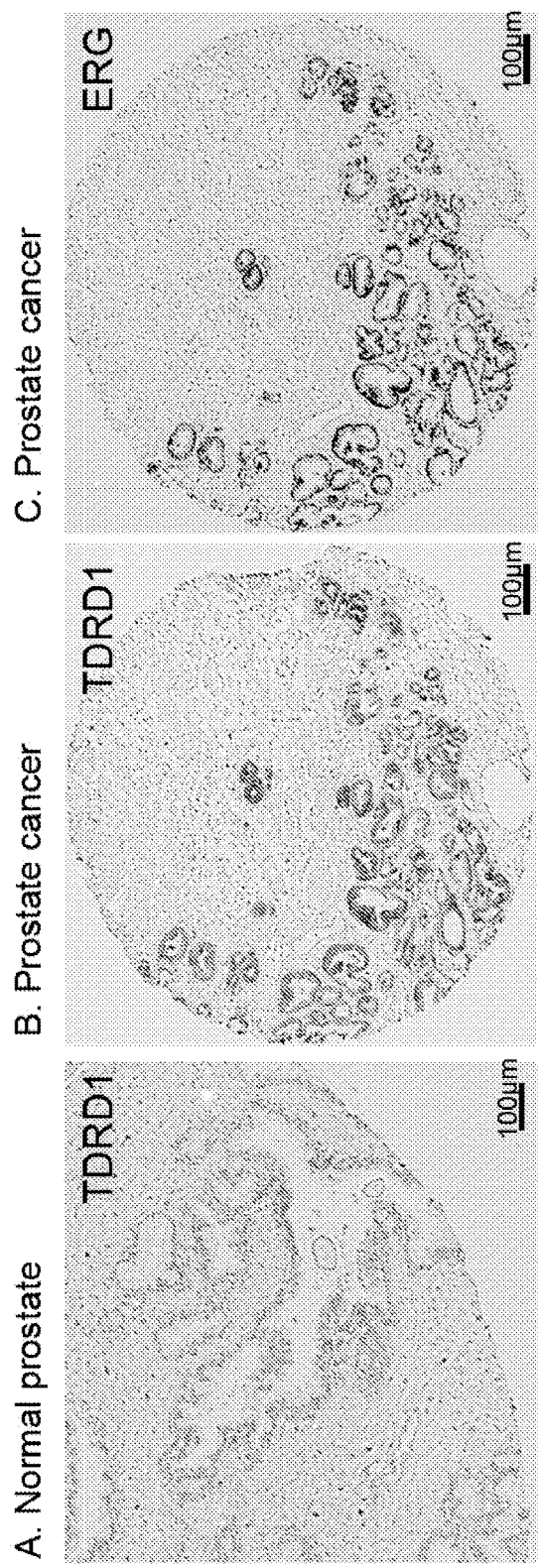
FIG. 9 demonstrates detection of TDRD1 by immunohistochemistry (IHC) in Formalin-Fixed, Paraffin-Embedded (FFPE) human prostate cancer sections, but not in normal prostate; (A) normal prostate; (B) prostate cancer using TDRD1 IHC; (C) prostate cancer using ERG IHC.

For Western Blot analysis, VCaP cells were treated with siNT (non-targeting control) or siTDRD1 for 3 days, and cell lysates were prepared. Shown in FIG. 5C, the exemplary mAb #1277 recognizes a band at130-140 kDa. This band is completely absent in TDRD1 knockdown cells, indicating that TDRD1 protein is indeed expressed in VCaP cells. IHC is performed on human prostate tumor specimen to determine if TDRD1 has prognostic value. FIG. 9 illustrates detection of TDRD1 by IHC in FFPE human prostate cancer sections, but there is no detectable TDRD1 in normal prostate samples.

EXAMPLE 8

Significance of Certain Prostate Cancer Embodiments

TDRD1 mRNA is not expressed in normal prostate, but is over-expressed in 68% of primary prostate tumors. Expression of TDRD1 in prostate tumors can be ERG-dependent and ERG-independent, in certain embodiments of the disclosure. TDRD1-positive primary prostate tumors had good prognosis and, therefore, TDRD1 is a clinically relevant prognostic marker for prostate tumors. TDRD1 protein (~130 kDa) is expressed in VCaP prostate cancer cells and the majority of human prostate tumor samples, but not in normal prostate tissues. Mouse monoclonal antibodies against human TDRD1 may be utilized as a diagnostic tool, in certain embodiments.

EXAMPLE 9

TDRD1 in Breast Cancer

Unbiased bioformatics analysis was performed on the publically available breast cancer database. TDRD1 mRNA levels are particularly enriched in Her2+ subgroup of breast cancer patients. In agreement with this observation, by Western blot analysis, TDRD1 protein is specifically detected in a subgroup of Her2+ breast cancer cell lines. These results indicate that TDRD1 is an important molecule in Her2+ breast cancer development.

Figure 7:
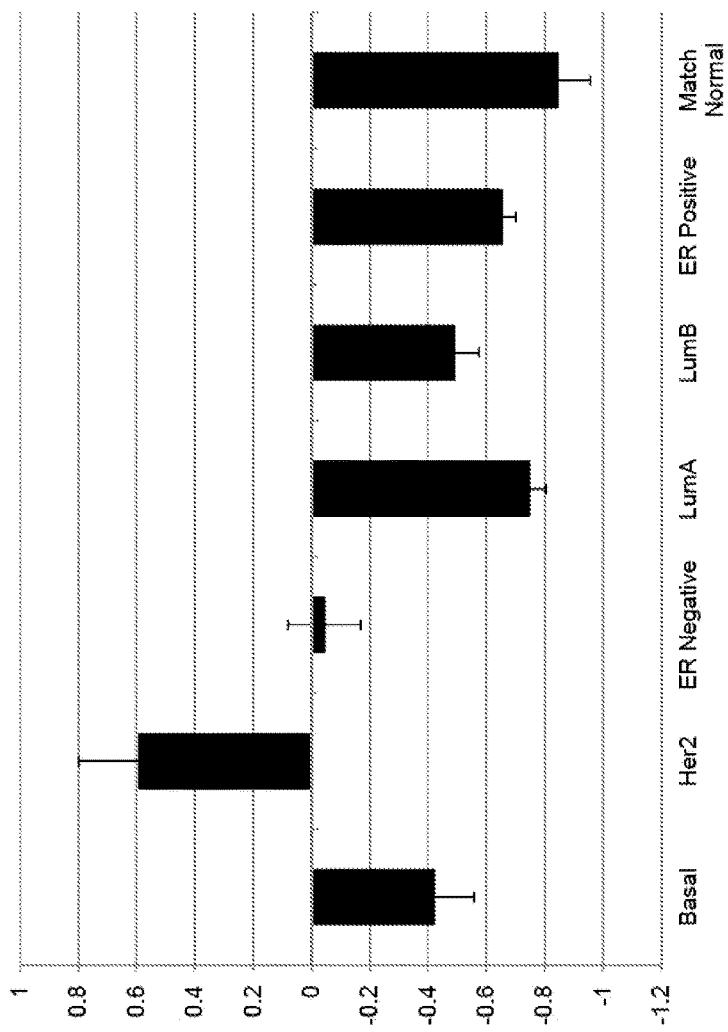
FIG. 7 demonstrates TDRD1 protein expression in a sub-group of breast cancer cell lines.

FIG. 7 shows TDRD1 average expression in Her2+ breast cancer.

Figure 8:
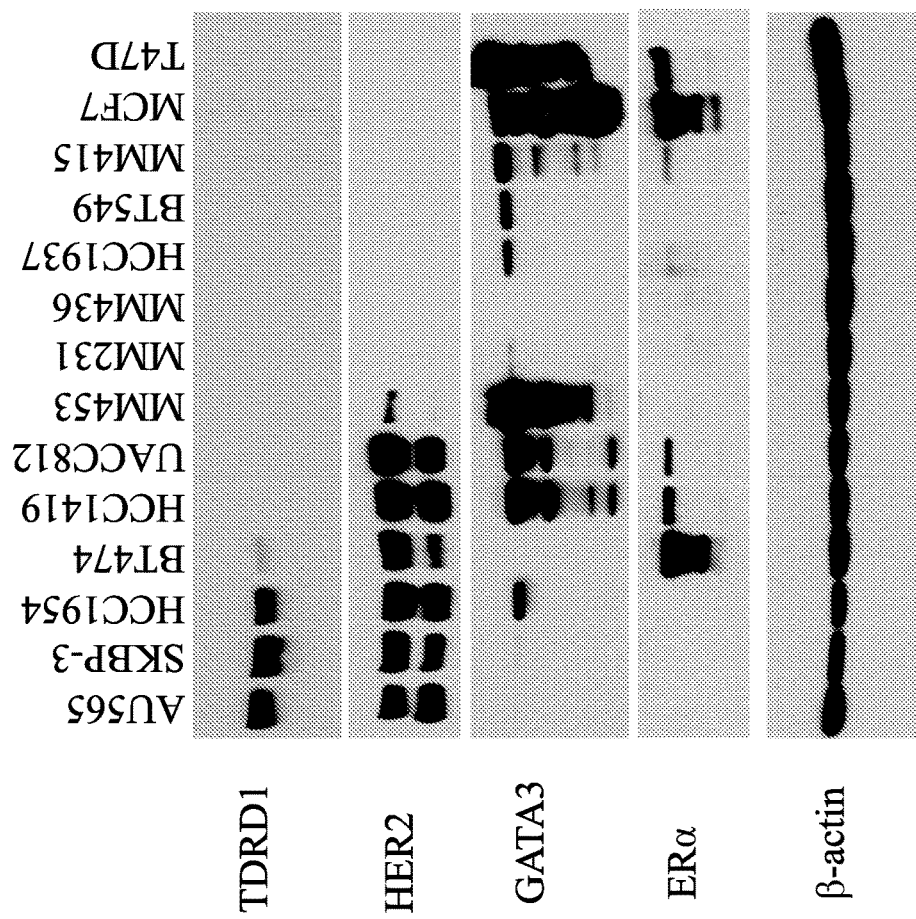
FIG. 8 demonstrates TDRD1 average expression in Her2+ breast cancer patients.

FIG. 8 shows TDRD1 expression in exemplary breast cancer cell lines.

FIG. 4 provides qPCR to show that TDRD1 is only expressed in human testis in normal tissues in men. VCaP cells was used as positive control. In FIG. 1B, from 18 prostate cancer patient RNA samples, each patient contains both normal and tumor prostate RNA samples. In these 18 patients, 13 of them are positive for both ERG and TDRD1.

FIG. 2 shows prognostic value of TDRD1 and ERG, based on statistical analysis of 127 untreated patients with primary prostate tumors. (A) TDRD1 positive tumors have good prognosis. (B) ERG alone has no prognosis value, in agreement with numerous reports. (C) a combination of TDRD1 and ERG expression provides better resolution, in at least some embodiments. In specific embodiments, TDRD1(+) ERG(−) patients have the best prognosis. At this time, there are not enough samples to consider prognosis for patients that are TDRD1 (−) ERG (+).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating an individual for cancer, comprising:
   treating an individual determined to be TDRD1-positive and ERG-negative from a sample from the individual with watchful waiting; or
   treating an individual determined to be TDRD1-negative and ERG-positive from a sample from the individual with a therapeutically effective amount of surgery, radiation, hormone therapy, chemotherapy, biologic therapy, or a combination thereof.

2. The method of claim 1, wherein the cancer is prostate cancer or breast cancer.

3. The method of claim 1, wherein the sample is blood, biopsy, or urine.

4. The method of claim 2, wherein the breast cancer is HER2+.

5. The method of claim 1, wherein the sample for assaying the TDRD1 level and the sample for assaying the ERG level are the same sample or are a different sample.

6. The method of claim 1, wherein the assaying step is further defined as comparing the level of expression of TDRD1 to a standard.

* * * * *